US00PP14149P39

(12) United States Plant Patent
Matsukizono

(10) Patent No.: US PP14,149 P3
(45) Date of Patent: Sep. 16, 2003

(54) PORTULACA PLANT NAMED 'KAKEGAWA CY2'

(75) Inventor: Hiromi Matsukizono, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 10/058,858

(22) Filed: Jan. 30, 2002

(65) Prior Publication Data

US 2003/0145364 P1 Jul. 31, 2003

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—Jondle & Associates P.C.

(57) ABSTRACT

Portulaca 'Kakegawa CY2' is a new variety of *Portulaca oleracea*. This plant has a vigorous, spreading plant growth which produces unique yellow color with purplish red streaks on the flowers.

1 Drawing Sheet

Genus and species: *Portulaca oleracea*.
Variety denomination: 'Kakegawa CY2'.

BACKGROUND OF THE NEW PLANT

This invention relates to a new and distinct cultivar of Portulaca plant, hereinafter referred to by the name 'Kakegawa CY2'. Portulaca 'Kakegawa CY2' is a new variety of *Portulaca oleracea*. The plant has a vigorous spreading growth habit and can be used as a groundcover. It can also be used in a potted or hanging basket presentation. The invention's flowers are a unique yellow color with purplish red streaks. The flowers are single and measure approximately 4.5 centimeters in diameter when fully open. The plant performs well in hot and dry climates. The plant is very resistant to rain, heat and drought.

ORIGIN AND ASEXUAL REPRODUCTION

The new cultivar is propagated asexually from vegetative cuttings. The asexual reproduction establishes that the plant does in fact maintain the characteristics described in successive generations. 'Kakegawa CY2' has been reproduced by stem cuttings in Salinas, Calif., and all of the characteristics thereof have been determined to be firmly fixed.

The new variety originated from a hybridization made in June, 1997 between the varieties 'Duet Yellow' (not patented) and 'Duet Rose' (not patented). $F_1$ seed was sown from this cross in February, 1998 and three plants were selected for having striped petals. Ten plants were vegetatively propagated from each selection. In June, 1998 and again in September, 1998 the plants from each selection were vegetatively propagated and evaluated for stability. One of the original selections was selected as the most appealing and most stable. This selection possessed predominantly yellow petals with numerous streaks of purplish red, a red pistil with red filaments and yellow anthers. In April, 1999 the selected line was vegetatively propagated again and stability of habit, color and petal striping was confirmed.

BRIEF DESCRIPTION OF DRAWINGS

The accompanying drawings serve by color photographic means to illustrate the new plant variety, 'Kakegawa CY2'. The colors are represented as true as possible using conventional photographic procedures.

DETAILED DESCRIPTION OF THE NEW VARIETY

Figure 2:
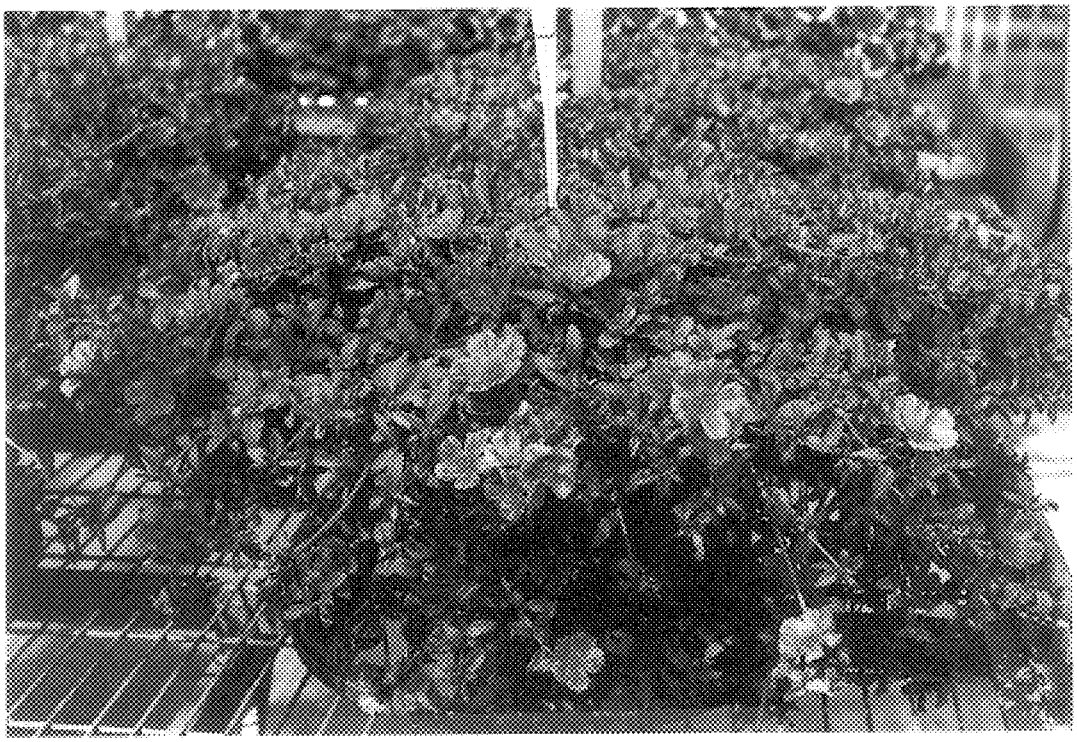
FIG. 2 is a view of several plants of the new cultivar growing in a 35.0 cm diameter pot.
Figure 1:
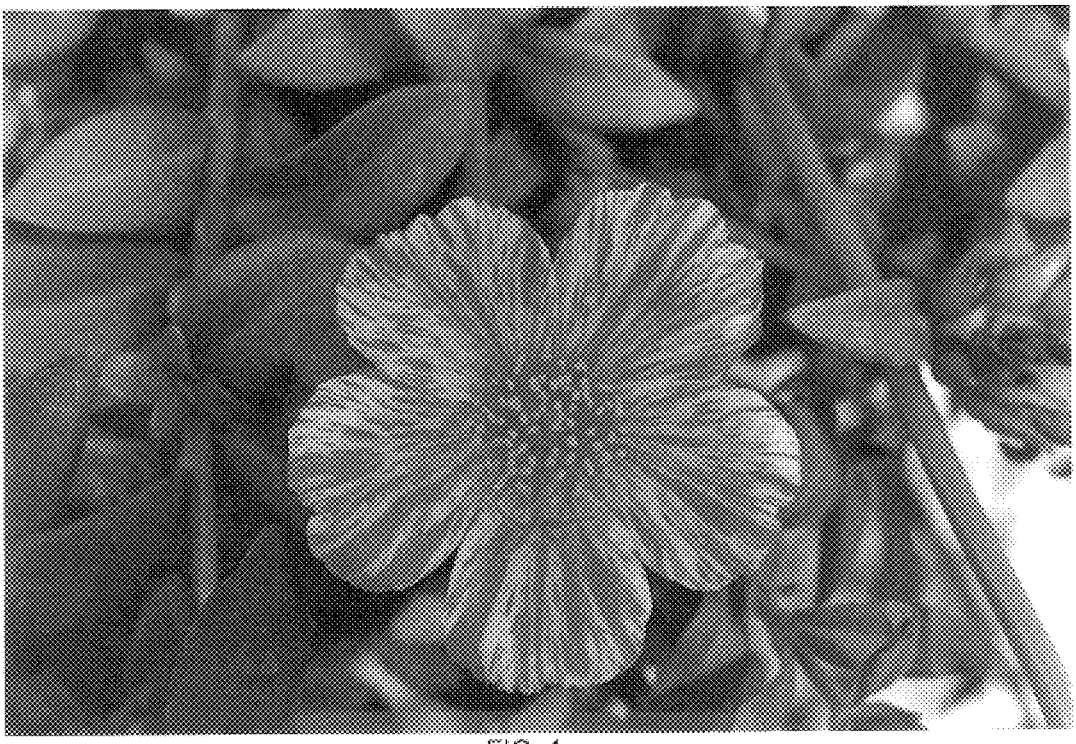
FIG. 1 is a close-up view of a 'Kakegawa CY2' flower illustrating its color and shape.

The following description is based on observations and measurements from 14–16 week old plants grown in 15 cm pots at Salinas, Calif. Plants were propagated from vegetative cuttings and grown in a glass greenhouse. These plants were grown in plastic pots containing a peat moss-based medium. Soluble fertilizer containing 18% nitrogen, 8% phosphorus and 18% potassium were applied every fourth irrigation. The plants were typically watered twice per week. Pots were topdressed with a slow release fertilizer containing 18% nitrogen, 8% phosphorus and 18% potassium. The average air temperature was 24° C.

Color designations were made according to The Royal Horticultural Society Colour Chart published by The Royal Horticultural Society of London, England.

Origin: Japan.
Parentage:
*Femal parent.*—'Duet Yellow' (not patented).
*Male parent.*—'Duet Rose' (not patented).
Classification:
*Family.*—Portulacaceae.
*Genus.*—Portulaca.
*Species.*—*oleracea.*
*Commercial.*—Portulaca/Purslane 'Kakegawa CY2'.
Plant:
*Growth habit.*—Prostrate.
*Plant height.*—23.0 cm.

*Spread.*—85 cm (in a six-inch pot) life cycle perennial.
*Time to produce a rooted cutting.*—2 weeks.
*Time to bloom from propagation.*—6–8 weeks.
*Time to produce a rooted cutting.*—Vegetative cuttings root in 7–10 days after sticking into a rooting medium like a peat moss based mix; the cuttings will form roots without the use of overhead mist.
*Flowering season/requirements.*—Spring to fall; flowers year round at temperatures of 24°–35° C.; day neutral light requirements.
*Temperature.*—Will not tolerate temperatures below 7° C.

Stem:
*Color.*—Yellowish green (144C).
*Anthocyanin.*—RHS 178B (greyed-red).
*Pubescence.*—Glabrous.
*Stem description.*—Round, slightly rough with lateral ridges.
*Diameter.*—5.0 mm.
*Length of internode.*—3.0–3.5 cm.

Leaf:
*Apex.*—Acute.
*Base.*—Rounded.
*Arrangement.*—Alternate; leaves appear whorled towards the apex where internodes are not elongated.
*Leaf color.*—Upper surface RHS 137C (green); lower surface RHS 138C (green).
*Anthocyanin.*—RHS 178B (greyed-red).
*Margin.*—Entire.
*Length (average).*—3.0 cm.
*Width (average).*—1.5 cm.
*Shape.*—Oblong.
*Thickness.*—1.0 mm.
*Texture.*—Smooth.
*Petiole color.*—RHS N144D (yellow-green).
*Petiole length.*—2.0 mm.
*Petiole diameter.*—2.0–3.0 mm.

Flower:
*Calyx.*—2 sepals; 1.0 cm×8.0 mm; free.
*Sepal shape.*—Elliptic.
*Sepal texture.*—Smooth.
*Sepal margin.*—Entire, slightly sinuate.
*Sepal apex shape.*—Cuspidate.
*Sepal color.*—The color gets lighter toward the margin until the tissue becomes transparent RHS 146C (yellow-green).
*Corolla.*—5 petals; free.
*Flower diameter.*—4.0–4.5 cm.
*Bud color.*—RHS 138B (green).
*Bud shape.*—Round and pointed at the top.
*Bud size.*—Length is 1.1–1.2 cm; diameter is 8 mm.
*Bud surface.*—Shiny.
*Duration of flower life.*—One day.
*Flowering habit.*—Determinate.
*Placenta arrangement.*—Central.
*Inflorescence type.*—Solitary, sessile.
*Stamens.*—50; approximately 1 cm in length; filament color RHS 63A (red-purple); anther color RHS 6C (yellow).
*Stigma.*—RHS 63A (red-purple).
*Pistils.*—1; branched on the top with 5 branches.
*Style.*—4.0–5.0 mm; RHS 63A (red-purple).
*Petal size.*—3.0×2.8–3.0 cm (l×w).
*Petal shape.*—Tri-lobed with inner lobe smaller than two outer lobes.
*Petal margin.*—Crenate.
*Petal apex shape.*—Retuse.
*Petal texture.*—Smooth and soft.
*Petal color.*—Upper surface RHS 13B (yellow) with RHS 70A (red-purple; lower surface RHS 13B (yellow) with RHS 70A (red-purple); base of petal inner surface RHS 13B (yellow); outer surface RHS 70A (red-purple). The petals are irregularly variegated yellow and pink with streaks running throughout the length of the petal. The percentage of the petal surface that is striped with pink color varies from flower to flower and between petals of the same flower. The width of the striping is irregular; i.e., the pink color can be "thick" so as to obviously show the yellow in the petal surface, or the pink color can be "wide" so as to cause a high percentage of the leaf as pink.
*Produces seed.*—No.
*Habit.*—The flowers bloom during midmorning and close at night. Each flower blooms only once and are produced throughout the growing season. The plants produce flowers regardless of day length; the plants are day neutral. Plants can have 40 to 50 open flowers at one time and have no fragrance.
*Hardiness.*—Plant is heat tolerant; thrives in heat and humidity; plant is not cold tolerant or below 7° C.

DISEASE AND INSECT RESISTANCE

No unusual susceptibility to diseases or insects have been observed.

COMPARISON WITH OTHER KNOWN VARIETIES

'Kakegawa CY2' is most similar to the variety 'Duet Yellow' (not patented). Both plants have similar habit and foliage, however 'Kakegawa CY2' has more stem anthocyanin color than 'Duet Yellow'. Additionally, where 'Duet Yellow' has yellow petals with a rose margin and fine streaks of purplish red, 'Kakegawa CY2' has yellow petals with numerous thicker purplish red streaks.

We claim:

1. A new and distinct Portulaca plant as shown and described herein.

* * * * *